United States Patent [19]

van Andel

[11] Plant 4,930

[45] Nov. 9, 1982

[54] ALSTROEMERIA NAMED STABLACO

[75] Inventor: Jacob van Andel, Aalsmeer, Netherlands

[73] Assignees: B. V. Handelskwekerij; M. C. van Staaveren, both of Aalsmeer, Netherlands

[21] Appl. No.: 226,812

[22] Filed: Jan. 21, 1981

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—C. W. Rummler

[57] ABSTRACT

A new variety of alstroemeria plant distinguished by its continuous production of slightly off-white blossoms of medium size, the upper petals of which have longitudinal rows of narrow, dark brown, pencil stripe spots appearing on a yellow background and extending from a pinkish base or flower throat; and by its strong, upright and very rapid growth habit reaching an average height of about two meters.

1 Drawing Figure

BACKGROUND OF THE NEW PLANT

My alstroemeria plant originated as a seedling resulting from my crossing of unnamed and unpatented alstroemeria varieties maintained as breeding stock in nursery facilities at Aalsmeer, The Netherlands. I selected this plant for propagation because of its unusual, almost pure white flowers highlighted by the upper petals which have brown pencil stripe streaks extending over a yellow background from a pink throat or base and reproduction was done by me at Aalsmeer by dividing the roots of the discovery plant. Continued propagation of this new plant through successive generations, by dividing root stock, has demonstrated that the novel characteristics of the new plant hold true from generation to generation and appear to be firmly fixed.

DESCRIPTION OF THE DRAWING

This new variety of alstroemeria plant is illustrated by the accompanying photographic drawing which, in full color, shows a branch of the plant in full bloom with both fully opened flowers and buds appearing in the view, the color rendition being as true as it is reasonably possible to obtain by conventional photographic procedures.

DESCRIPTION OF THE NEW PLANT

The following is a detailed description of my new alstroemeria plant with color designations according to The R.H.S. Colour Chart of The Royal Horticultural Society of London, England.

THE PLANT

Origin: Seedling.

Parentage:

*Seed parent.*—Ed. (unpatented).

*Pollen parent.*—No. 2171-1 (unpatented). These varieties are maintained in stock at Aalsmeer, The Netherlands, and are identified by the above designations in my breeding records.

Classification:

*Botanic.*—Alstroemeria.

*Commercial.*—Hybrid Alstroemeria.

Form: Bush, comprising tall, slender, flowering stalks, each with flower bearing stems in simple umbel arrangement at its top.

Height: About 2 meters.

Growth: Strong, vigorous and upright.

Growth rate: Fast.

Root stock: Tuberous. The tubers bear many buds during the year from which flower stalks appear in various stages of development during the course of the year.

Foliage:

*Quantity.*—Medium.

*Leaf size.*—About 16 cm. long and 3 cm. wide.

*Leaf shape.*—Elliptic.

*Texture.*—Smooth.

*Color.*—Upper side — Green. Under side — Green/Grey.

THE BUD

Size: About 2 cm. long and 1 cm. in diameter.

Form: Ovoid.

Color: When petals begin to unfurl — RHS 158C-D.

THE FLOWER

Blooming habit: Continuous.

Flower size: Medium.

*Diameter.*—About 5.5 to 6 cm.

*Depth.*—About 5 cm.

Shape: Generally cup-shaped and this form does not change.

Borne: Singly on a long peduncle or stem.

Petalage:

*Number of petals.*—6.

*Arrangement.*—Two concentric circles of three petals each.

*Form.*—Wide, elliptic.

*Color.*—Petal body — 158C-D. Stripes on upper petals — 176A. Petal base — Pink 48D. Reverse side — Pink 48D.

*Texture.*—Soft.

*Appearance.*—Shiny.

Persistence: The flower does not hang on.

Peduncle: Sturdy and upright.

*Length.*—About 4 cm.

*Color.*—Green.

Lasting quality:

*On plant.*—About 21 days.

*As a cut flower.*—About 14 days.

REPRODUCTIVE ORGANS

Stamens:

*Number.*—Six.

*Arrangement.*—Two circles of three, one opposite each petal.

*Filaments.*—Length: about 4 cm. Pollen color: Grey/Green.

Pistils:

*Number.*—Three.

*Length.*—About 4½ to 5 cm.

Stigmas:

*Color.*—Orange.

Fruit:

*Fertility.*—No.

*Shape.*—Ovoid.

*Color at maturity.*—Green/Brown.

I claim:

1. The new and distinct variety of alstroemeria plant, substantially as herein shown and described, characterized by the distinctive off-white principal coloring of the flowers, and the rows of dark brown pencil stripe spots appearing on a yellow background and extending from the flower throat.

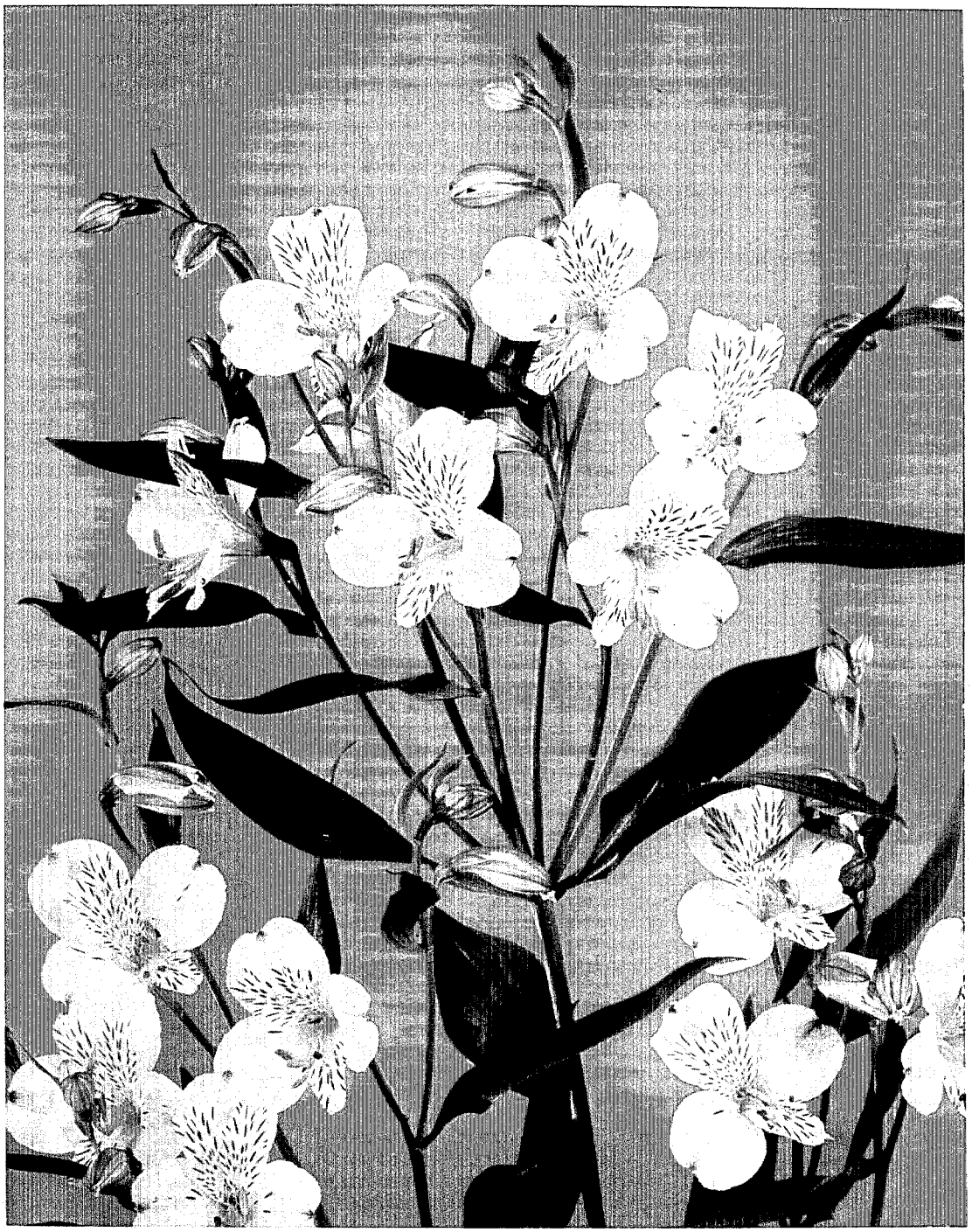

* * * * *